US010010694B2

(12) United States Patent
Lin (10) Patent No.: US 10,010,694 B2
(45) Date of Patent: Jul. 3, 2018

(54) GAS GENERATING SYSTEM FOR HEALTH USE (71) Applicant: Hsin-Yung Lin, Taoyuan (TW)

(72) Inventor: Hsin-Yung Lin, Taoyuan (TW)

( * ) Notice: Subject to any disclaimer, the term of this patent is extended or adjusted under 35 U.S.C. 154(b) by 440 days.

(21) Appl. No.: 14/590,048

(22) Filed: Jan. 6, 2015

(65) Prior Publication Data

US 2015/0190604 A1 Jul. 9, 2015

(30) Foreign Application Priority Data

Jan. 7, 2014 (CN) .......................... 2014 1 0008689

(51) Int. Cl.
*A61M 16/12* (2006.01)
*A61M 16/08* (2006.01)
*C25B 1/04* (2006.01)
*A61M 16/16* (2006.01)
*A61M 16/00* (2006.01)
A61M 16/20 (2006.01)
A61M 16/06 (2006.01)

(52) U.S. Cl.
CPC ...... *A61M 16/122* (2014.02); *A61M 16/0003* (2014.02); *A61M 16/0833* (2014.02); *A61M 16/16* (2013.01); *C25B 1/04* (2013.01); A61M 16/06 (2013.01); A61M 16/0875 (2013.01); A61M 16/20 (2013.01); A61M 2016/003 (2013.01); A61M 2202/0208 (2013.01); A61M 2202/0468 (2013.01); A61M 2205/3334 (2013.01); Y02E 60/366 (2013.01)

(58) Field of Classification Search
CPC .... A61M 11/005; A61M 16/00; A61M 16/10; A61M 16/1005; A61M 16/122; A61M 16/14; A61M 16/147; A61M 16/0833; A61M 16/0875; C25B 1/04–1/12
See application file for complete search history.

(56) References Cited

U.S. PATENT DOCUMENTS 3,397,693 A * 8/1968 Ernst .................... A62B 7/00
128/204.28
3,917,520 A * 11/1975 Katz .................... C25B 1/04
204/274
5,865,171 A * 2/1999 Cinquin ............... A61M 11/005
128/200.14

(Continued)

FOREIGN PATENT DOCUMENTS

CN     1161236 A     10/1997
CN     102847213 A    1/2013

(Continued)

*Primary Examiner* — Valerie L Woodward (57) ABSTRACT

A gas generating system for health use is provided, including a hydrogen-oxygen gas generator and an atomized/volatile gas generator. The hydrogen-oxygen gas generator has a first casing. The first casing accommodates an electrolysis device for electrolyzing water in order to produce a gas mixture of hydrogen and oxygen. The atomized/volatile gas generator has a second casing, the second casing accommodates a gas mixing camber coupled to the electrolysis device to receive and combine the gas mixture of hydrogen and oxygen with water vapor, an atomized medicine, a volatile essential oil or any combination thereof in order to produce a healthy gas for a user to inhale.

9 Claims, 5 Drawing Sheets (56) References Cited

U.S. PATENT DOCUMENTS

| | | | | |
|---|---|---|---|---|
| 2004/0146759 | A1* | 7/2004 | Hecker | B01D 53/326 205/343 |
| 2005/0136299 | A1* | 6/2005 | Richey, II | A61M 16/10 205/628 |
| 2007/0135757 | A1* | 6/2007 | Acker | A61M 16/0666 604/26 |
| 2013/0206586 | A1* | 8/2013 | Lin | C25B 15/02 204/228.2 |
| 2014/0378745 | A1* | 12/2014 | Lin | C25B 9/06 600/27 |
| 2015/0144132 | A1* | 5/2015 | Satoh | A61M 16/0057 128/202.26 |

FOREIGN PATENT DOCUMENTS

| | | |
|---|---|---|
| CN | 203291353 U | 11/2013 |
| CN | 203291354 U | 11/2013 |
| JP | S62202805 A | 9/1987 |
| JP | 2003013269 A | 1/2003 |

\* cited by examiner

GAS GENERATING SYSTEM FOR HEALTH USE

BACKGROUND OF THE INVENTION

1. Field of the Invention

The present invention relates to a gas generating system for health use, more particularly, a gas generating system for health use that generates a gas mixture of hydrogen and oxygen.

2. Description of the Prior Art

Since the beginning of time, figuring out methods for preserving life has always been a high priority. Many developments in medical technology are used to treat diseases and increase life expectancy. In the past, most medical treatments were passive. In other words, diseases were treated only when people fell ill, through surgical operations, medication, chemotherapy, radiation treatment and so on. It wasn't until recently that many medical experts began focusing on disease prevention, such as studying healthy foods and screening for inherited diseases to actively reduce the risk of becoming ill. Furthermore, in order to increase life expectancy, many anti-aging technologies have been developed, including skin care products, antioxidant food/medicine and so on.

In recent years, people have begun to notice the benefits of aromatherapy. Aromatherapy is a natural way to allow people to feel relaxed while at the same time becoming healthier. Essential oils are extracted from aromatic plants to act as a medium, which is then exposed to someone through massaging, bathing, perfumes, etc. The methods of aromatherapy have existed since the ancient times of Egypt and are now gaining a lot of attention in Europe. A French scientist published his research results on aromatherapy in a scientific journal, which then sparked interest in many people. His research found that the plant's essential oils have the ability to reach deep tissue layers of the skin, which is then absorbed by blood vessels and goes to organs that need to be treated with blood circulation.

Therefore, the present invention provides a gas generating system for health use. The gas generator can produce a healthy gas for health care use that allows people to feel relaxed and is also suitable to be used in medical treatments.

SUMMARY OF THE INVENTION

One aspect of the present invention is to provide a gas generating system for health use. The gas generating system for health use can generate a healthy gas comprising a gas mixture of hydrogen and oxygen to be being inhaled by a user.

According to an embodiment of the present invention, the gas generating system for health use comprises a hydrogen-oxygen gas generator, an atomized/volatile gas generator, and a connector group. The hydrogen-oxygen gas generator has a first casing. The first casing is accommodated with an electrolysis device that electrolyzes water to produce a gas mixture containing hydrogen and oxygen. The atomized/volatile gas generator has a second casing. The second casing is accommodated with an atomized/volatile gas mixing tank to generate an atomized gas. The atomized gas is selected from a group comprising water vapor, an atomized medicine, a volatile essential oil or any combination thereof. The connector group is coupled to the atomized/volatile gas generator and the hydrogen-oxygen gas generator, so that the gas mixture of hydrogen and oxygen is mixed with the atomized gas in order to generate a healthy gas. The healthy gas is then provided to a user to be inhaled.

According to another embodiment of the present invention, the hydrogen-oxygen gas generator further comprises a humidifier. The humidifier is configured in the first casing and connected to the electrolysis device and is used to receive the gas mixture of hydrogen and oxygen in order to generate a filtered gas mixture of hydrogen and oxygen, where the healthy gas is then mixed with the atomized gas and the filtered gas mixture of hydrogen and oxygen.

According to another embodiment of the present invention, the hydrogen-oxygen gas generator is adapted to selectively further comprise a conversion valve. The conversion valve is configured between the humidifier and the atomized/volatile gas generator and is adapted to be selectively connected from the humidifier to the atomized/volatile gas generator so that the atomized gas is mixed with the filtered gas mixture of hydrogen and oxygen in order to generate the healthy gas. The conversion valve can also be adapted to be selectively disconnected from the humidifier and the atomized/volatile gas mixing tank so that the filtered gas mixture of hydrogen and oxygen is directly outputted from the first casing and provided to be inhaled by the user.

The atomized/volatile gas generator is then adapted to selectively comprise an oscillator. The oscillator is used to atomize or vaporize a liquid in order to generate the atomized gas. Furthermore, the liquid is adapted to be selected from a group comprising an essential oil, a medicinal liquid, pure water or any combination thereof.

At the same time, the atomized/volatile gas generator is adapted to selectively comprise an atomized base liquid. The liquid is set above the atomized base liquid, and the oscillator is set under the atomized base liquid.

At the same time, the gas generating system for health use of the present invention is adapted to selectively comprise a flow rate detection device. The flow rate detection device is coupled to the electrolysis device to detect the flow rate of the gas mixture of hydrogen and oxygen and controlling the production capacity of the gas mixture of hydrogen and oxygen comprised in the electrolysis device. The flow rate detection device is adapted to selectively shut down an input voltage or an input current of the electrolysis device.

The gas generating system for health use of the present invention is then adapted to selectively comprise a mask, wherein the connector group comprises a first pipe and a second pipe. The first pipe is configured between the atomized/volatile gas generator and the hydrogen-oxygen gas generator to transport the gas mixture of hydrogen and oxygen from the hydrogen-oxygen gas generator to the atomized/volatile gas generator. The second pipe is configured between the second pipe and the mask to transport the healthy gas from the atomized/volatile gas generator to the mask and outputting the healthy gas through the mask.

According to another embodiment of the present invention, the gas generating system for health use of the present invention is adapted to selectively comprise a mask, wherein the connector group comprises a third pipe, a fourth pipe and a mixed kit. The third pipe is configured between the mixed kit and the hydrogen-oxygen gas generator to transport the gas mixture of hydrogen and oxygen from the hydrogen-oxygen gas generator to the mixed kit. The fourth pipe is configured between the mixed kit and the atomized/volatile gas generator to transport the hydrogen-oxygen gas generator from the hydrogen-oxygen gas generator to the mixed kit. The mixed kit mixes the gas mixture of hydrogen and oxygen and the atomized gas to generate the healthy gas and outputting the healthy gas through the mask.

The gas generating system for health use according to the present invention can generate a gas mixture of hydrogen and oxygen, where the gas mixture can then be selectively mixed with an atomized medicine, water vapor, a volatile essential oil, or any combination thereof in order to form a healthy gas to be inhaled by a user. As the healthy gas includes a certain concentration of hydrogen, it provides anti-oxidation and anti-aging effects. In addition, the atomized medicine in the healthy gas can be easily absorbed into a user. Furthermore, the volatile essential oil in the healthy gas can relieve stress and improve the health of its users.

Many other advantages and features of the present invention will be further understood by the following detailed description and the appended drawings.

BRIEF DESCRIPTION OF THE APPENDED DRAWINGS

To facilitate understanding, identical reference numerals have been used, where it is possible to designate identical elements that are common to the figures.

DETAILED DESCRIPTION OF THE INVENTION

In order to allow the advantages, spirit and features of the present invention to be more easily and clearly understood, the embodiments and appended drawings thereof are discussed in the following. However, the present invention is not limited to the embodiments and appended drawings.

Figure 1:
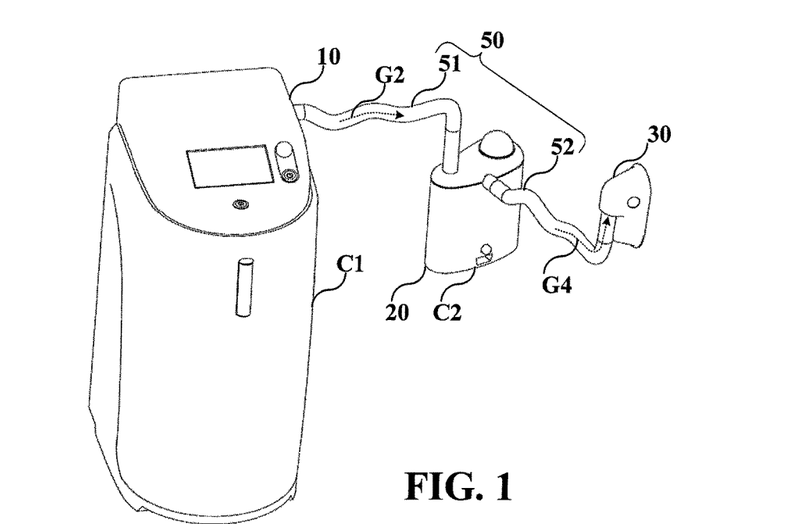
FIG. 1 is a schematic diagram illustrating a gas generating system for health use according to one embodiment of the present invention.

Please refer to FIG. 1. FIG. 1 is a schematic diagram illustrating a gas generating system for health use according to one embodiment of the present invention. The gas generating system for health use 1 of the present invention comprises a hydrogen-oxygen gas generator 10, an atomized/volatile gas generator 20, a gas output device 30, and a connector group 50. In the present embodiment, the hydrogen-oxygen gas generator 10 and the atomized/volatile gas generator 20 separately have a first casing C1 and a second casing C2. The first casing C1 and the second casing C2 are connected to each other through a first pipe 51 of the connector group 50 to transport gas.

In application, the hydrogen-oxygen gas generator 10 is used for electrolyzing water in order to produce a gas mixture of hydrogen and oxygen G1. A filtered gas mixture of hydrogen and oxygen G2 is generated from the gas mixture of hydrogen and oxygen filtered through the humidifier. Then the filtered gas mixture of hydrogen and oxygen G2 can go through the atomized/volatile gas generator 20 to be mixed with an atomized gas G3 generated from the atomized/volatile gas generator 20, which is then transported to the gas output device 30 through a second pipe 52 of the connector group 50 and outputted from the gas output device 30. In the present embodiment, the gas output device 30 is a mask, but is not limited thereof. The gas output device 30 may be any device or equipment that is capable of outputting the above mixed gas and hence will not discussed in detail herein.

Figure 2:
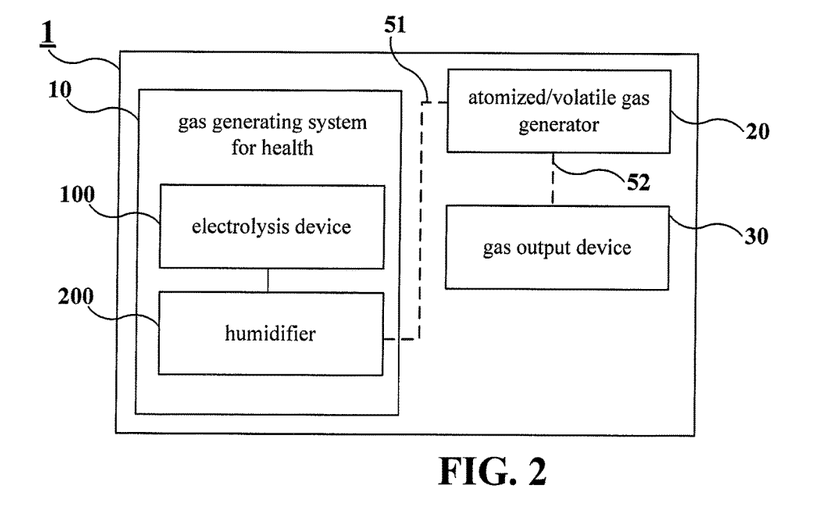
FIG. 2 is a functional block diagram illustrating a gas generating system for health use according to the present invention.

Please refer to FIG. 2. FIG. 2 is a functional block diagram illustrating a gas generating system for health use according to the present invention. As shown in the figure, the hydrogen-oxygen gas generator 10 of the present invention comprises an electrolysis device 100 and a humidifier 200. The detailed designs of the electrolysis device 100 and the humidifier 200 will be explained in the following.

Figure 3:
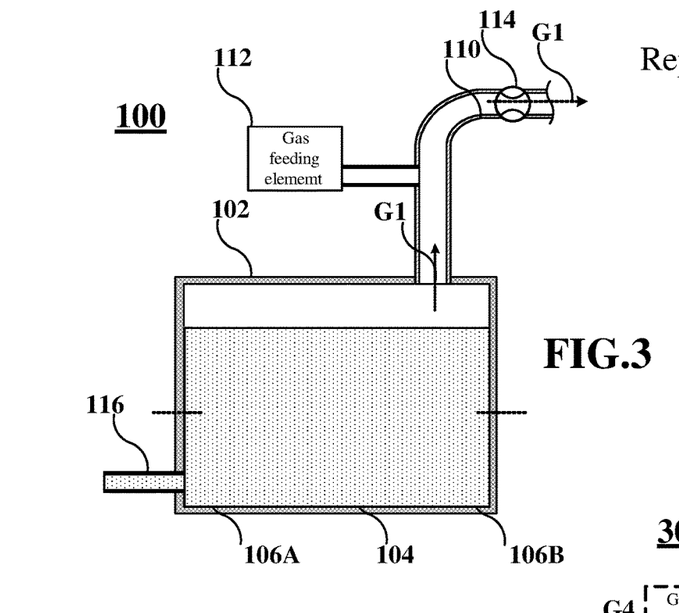
FIG. 3 is a schematic diagram illustrating an electrolysis device of a gas generating system for health use according to another embodiment of the present invention.

Please refer to FIG. 3. As shown in the figure, in some embodiments of the present invention, the electrolysis device 100 comprises an electrolysis tank 102 for accommodating electrolytic water 104. The main ingredient of the electrolytic water 104 is pure water, but electrolytes such as sodium hydroxide, calcium carbonate and sodium chloride can be added into the electrolyzed water 104 as needed. The electrolysis tank 102 further comprises two electrodes 106A and 106B, where the two electrodes 106A and 106B respectively represent a cathode electrode and an anode electrode. The two electrodes 106A and 106B are coupled to a power supply (not shown) to provide the required power for electrolyzing the water. In some embodiments, the polarity of the two electrodes 106A and 106B are fixed, for example, the electrode 106A is the cathode and the electrode 106B is the anode. In other embodiments of the present invention, the polarity of the two electrodes 106A and 106B can be alternated. For example, at a point in time, the electrode 106A is the cathode and the electrode 106B is the anode, but after a predetermined time, the electrode 106A changes into the anode and the electrode 106B changes into the cathode.

After the two electrodes 106A and 106B are powered, the water 104 in the electrolysis tank 102 will begin being electrolyzed in order to generate hydrogen and oxygen. Hydrogen is generated on the cathode and oxygen is generated on the anode, and both hydrogen and oxygen are released to the upper part of the electrolysis tank 102 in order to form a gas mixture of hydrogen and oxygen G1. The gas mixture of hydrogen and oxygen G1 is outputted from a gas line 110 of the electrolysis tank 102 to be used. In another embodiment, hydrogen from the cathode and oxygen from the anode are outputted to the electrolysis tank 102 through a gas pipe and then mixed in order to form the gas mixture of hydrogen and oxygen G1. The ratio of hydrogen to oxygen generated from the electrolysis of water is about 2:1 ($H_2$:$O_2$), wherein the proportion of the hydrogen in the combination gas may exceed 66%. In some embodiments, a gas feeding element 112 can be applied in the present invention to add a gas into the gas mixture of hydrogen and oxygen G1, in order to reduce the concentration of hydrogen to an amount. For example the concentration of hydrogen can be between 2% to 60%, such as an amount between 2% to 4%, wherein the gas can be air, an inert gas (such as nitrogen), oxygen, water vapor or any combination thereof. In another embodiment of the present invention, a flow controller 114 is configured in the gas line 110 to detect the gas flow. The magnitude of the voltage or the current (the magnitude of the power) in the electrolysis tank 102 is adjusted according to the gas flow in order to control the gas production, so that the concentration of hydrogen in the gas mixture of hydrogen and oxygen G1 can be reduced when the gas mixture of hydrogen and oxygen G1 is transferred to a downstream device and mixed with the gas in the downstream device. The method for adjusting the magnitude of the voltage or the current in the electrolysis tank 102 can also comprise the method of cutting off the voltage or the current in the electrolysis tank 102. For example, when the flow rate detection device 114 senses an abnormal level from the gas mixture of hydrogen and oxygen generated from inside the electrolysis tank, such as sensing when the gas flow is greater or less than a predetermined gas flow rate, the flow rate detection device 114 will cut off the power being supplied to the electrolysis device. It is worth noting that the above gas feeding element 112 and the flow rate detection device 114 can be selectively used, namely simultaneously used, alternatively used, or completely unused, and can be replaced by any other apparatus that can reduce the concentration of hydrogen. In other embodiments, the flow rate detection device 114 in the gas line 110 can be selectively replaced by a flow controller to control the output flow comprising the gas mixture of hydrogen and oxygen G1, so that the concentration of hydrogen in the gas mixture of hydrogen and oxygen G1 can be reduced when the gas mixture of hydrogen and oxygen G1 is transferred to the downstream device and mixed with the gas in the downstream device.

Figure 4:
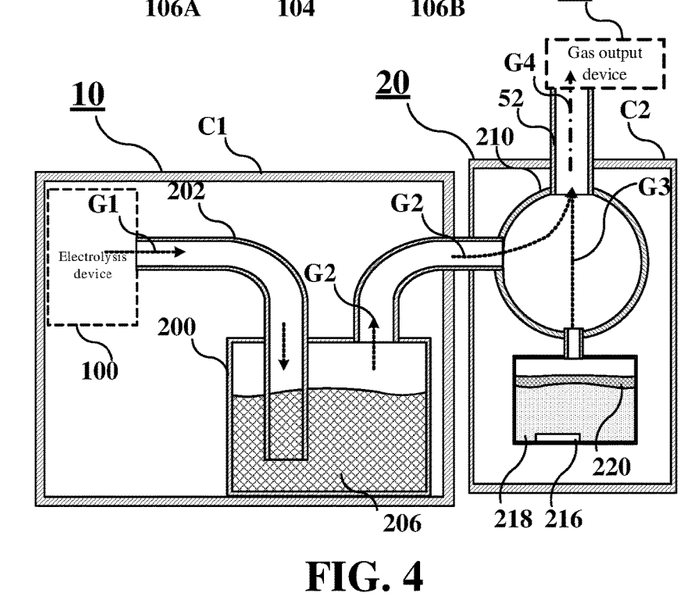
FIG. 4 is a schematic diagram illustrating a gas generating system for health use according to one embodiment of the present invention.

Now please refer to FIG. 4. FIG. 4 is a schematic diagram illustrating a gas generating system for health use according to one embodiment of the present invention. As shown in the figure, the humidifier 200 is coupled to the electrolysis device 100 in FIG. 3. For example, a pipe is coupled to the gas line 110 of the electrolysis device 100 in FIG. 3 to receive the gas mixture of hydrogen and oxygen G1. The humidifier 200 comprises something such as a sink or a pure water tank, to filter the gas mixture of hydrogen and oxygen G1 with water or pure water 206, thereby generating the filtered gas mixture of hydrogen and oxygen G2. In some embodiments, the humidifier 200 is adapted to filter out other gases, such as chlorine, from the gas mixture of hydrogen and oxygen G1 excluding hydrogen and oxygen. Therefore, the humidifier 204 is not limited to the pure water tank in this embodiment and can be any type of apparatus which can be adapted to absorb gases or impurities besides hydrogen and oxygen.

Next, please refer to FIG. 1 and FIG. 4. In the present embodiment of the present invention, the filtered gas mixture of hydrogen and oxygen G2 is transported to the atomized/volatile gas generator 20 through the first pipe 51 configured between the atomized/volatile gas generator 20 and the hydrogen-oxygen gas generator 10 to be used.

The design of the atomized/volatile gas generator 20 will be described in the following. In the present embodiment of the present invention, the atomized/volatile gas generator 20 comprises an oscillator 216 to atomize or vaporize a liquid 218 and a liquid 220, thereby generating the atomized gas G3, which is then mixed in an atomized/volatile gas mixing tank 210. The liquid 218 can be pure water to serve as an atomized base liquid. The liquid 220 can be an essential oil, a medicinal liquid, pure water or any combination thereof. Therefore, the atomized gas G3 can be a volatile essential oil, an atomized medicine, water vapor, or any combination thereof. More particularly, the atomized/volatile gas mixing tank 210 in the atomized/volatile gas generator 20 is adapted to mix the gasified liquid 218 and the gasified liquid 210 to generate the atomized gas G3. At the same time, the liquid 220 can be set above the atomized base liquid, while the oscillator 216 can be set below the atomized base liquid.

In application, the filtered gas mixture of hydrogen and oxygen G2 can be transported to the atomized/volatile gas generator 20 through a first pipe, where the filtered gas mixture of hydrogen and oxygen G2 can then be mixed with the atomized gas G3 to generate a healthy gas G4, where it is then transported to the gas output device 30 through the second pipe 52 of the connector group 50 for user use.

Figure 5:
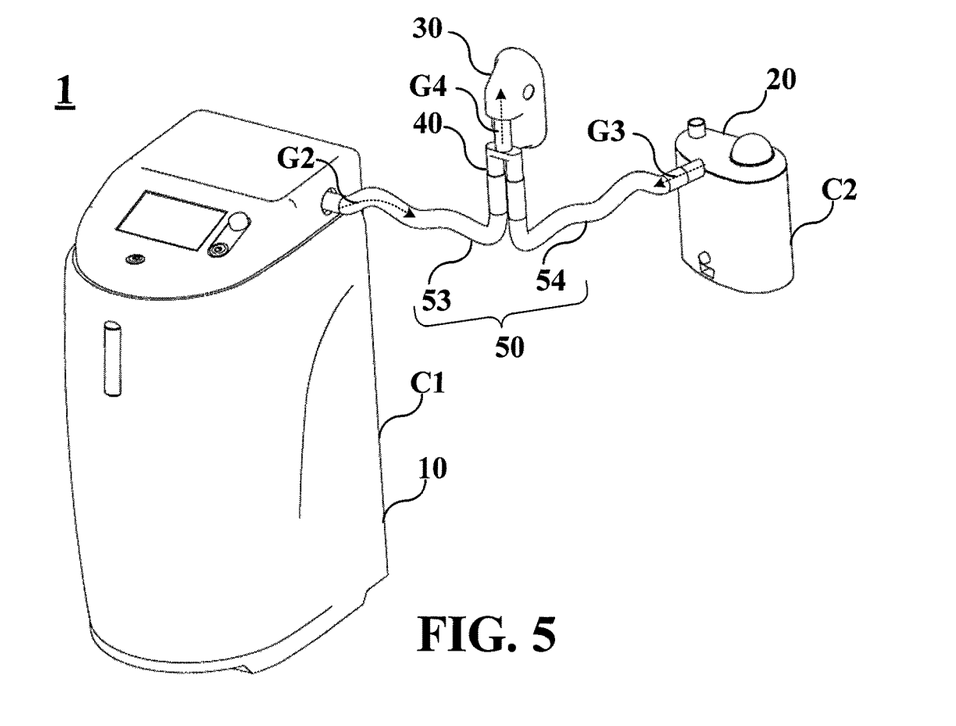
FIG. 5 is a schematic diagram illustrating a gas generating system for health use according to one embodiment of the present invention.

Please refer to FIG. 5. The hydrogen-oxygen gas generator 10 and the atomized/volatile gas generator 20 are connected to a mixed kit 40 through a third pipe 53 and a fourth pipe 54 of the connector group 50 respectively as shown in the figure. The mixed kit 40 can mix the gas mixture of hydrogen and oxygen G2 inputted from the hydrogen-oxygen gas generator 10 and the atomized gas G3 inputted from the atomized/volatile gas generator 20 where the above mix is then outputted through the gas output device 30 for a user to use.

Figure 6:
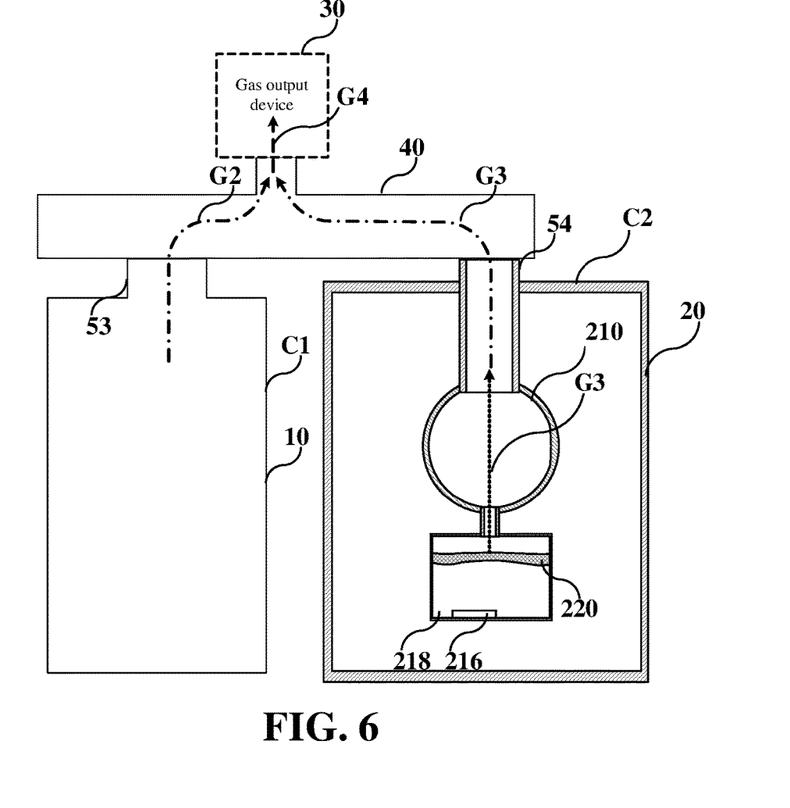
FIG. 6 is a schematic diagram illustrating an atomized/volatile gas generator of a gas generating system for health use according to one embodiment of the present invention.

In the present embodiment of the present invention, the design of the atomized/volatile gas generator 20 also needs a corresponding adjustment. Please refer to FIG. 6. FIG. 6 is a schematic diagram illustrating an atomized/volatile gas generator of a gas generating system for health use according to another embodiment of the present invention. Compared to the design in FIG. 4, the atomized/volatile gas mixing tank 210 in the atomized/volatile gas generator 20 of the present invention is only used to mix the gasified liquid 218 and the gasified liquid 210 in order to generate the atomized gas G3 and cannot be directly connected to the humidifier 200 to input the filtered gas mixture of hydrogen and oxygen G2. The atomized gas G3 and the filtered gas mixture of hydrogen and oxygen G2 would instead be mixed in the mixed kit 40 and transported to the gas output device 30 for a user to use.

Figure 7:
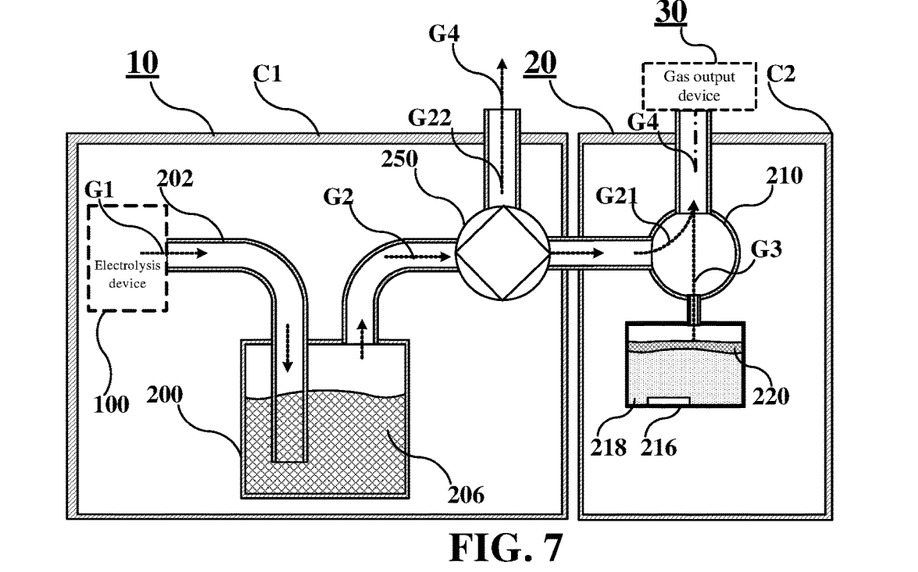
FIG. 7 is a schematic diagram illustrating a gas generating system for health use according to another embodiment of the present invention.

Next, please further refer to FIG. 7. FIG. 7 is a schematic diagram illustrating a gas generating system for health use according to another embodiment of the present invention, which differs from FIG. 4 in that the hydrogen-oxygen gas generator 10 of the present embodiment further comprises a conversion valve 250. The conversion valve 250 is configured between the humidifier 200 and the atomized/volatile gas mixing tank 210, wherein the conversion valve 205 is adapted to selectively connect the humidifier 204 to the atomized/volatile gas mixing tank 210 in order for the atomized gas G3 to mix with the filtered gas mixture of hydrogen and oxygen G21 in order to generate the healthy gas G4. The conversion valve is also adapted to selectively disconnect the humidifier from the atomized/volatile gas mixing tank 210 so that the filtered gas mixture of hydrogen and oxygen G2 is directly outputted in order to generate the healthy gas G4. In other words, the user has a choice in deciding whether or not the healthy gas should include the volatile essential oil, the atomized medicine or water vapor by switching the conversion valve. Whereby in this embodiment of the present invention, the gas output device 30 is configured to the outlet of the conversion valve 250. This embodiment of the present invention is different from the embodiment of FIG. 1 in that this embodiment allows the user to selectively inhale the healthy gas G4 that only includes the gas mixture of hydrogen and oxygen.

In another embodiment of the present invention, the user can decide the composition of the healthy gas using other ways, such as by turning on/off the oscillator 216. For example, if the oscillator 216 is turned on, the filtered gas mixture of hydrogen and oxygen G2 will be mixed with the atomized gas G3 in order to generate the healthy gas G4; if the oscillator 216 is turned off, the atomized gas G3 will not be generated and the healthy gas G4 will only contain the filtered gas mixture of hydrogen and oxygen G2. The filtered gas mixture of hydrogen and oxygen G2 can be selectively outputted from the hydrogen-oxygen gas generator 10 by turning on/off the oscillator 216 in order to form the healthy gas G4 to be inhaled by the user.

According to the above embodiments of the present invention, the healthy gas G4 comprises hydrogen and oxygen, and optionally water vapor, a volatile essential oil, an atomized medicine, or a combination thereof in order to form a healthy gas to be inhaled by a user (not shown). Studies have found that there is an instable oxygen species (O+), also known as free radicals, in the human body. The free radicals are usually created due to diseases, diet, environment and one's lifestyle, and the free radicals can be excreted in the form of water by reacting with the inhaled hydrogen. With this method, the amount of free radicals in the human body can be reduced, thereby restoring the body condition from an acidic state to an alkaline state, which can achieve an anti-oxidation, anti-aging and beauty health effect, and even eliminating chronic diseases. In addition, according to clinical studies, the atomized medicinal liquid is 1-5 micro meters and is easier absorbed by the human body than its non-atomized counterpart. That is to say, compared with its non-atomized counterpart, the atomized medicine can achieve the same therapeutic effect with a much lower dosage amount. Furthermore, the drug's side effects can be reduced due to the low dosage amount of atomized medicine administered. Therefore, the healthy gas 214 may provide an excellent therapeutic effect. There are also clinical experiments showing that patients who need to inhale a high concentration of oxygen for a long time are prone to lung damage from the high concentration of oxygen but can be ameliorated by inhaling hydrogen. Aside from those benefits, the volatile essential oil in the healthy gas can help general users relieve stress and improve health.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the meets and bounds of the appended claims.

What is claimed is:
1. A gas generating system for health use, comprising:
   a gas generator, having a first casing, the first casing accommodated with an electrolysis device for electrolyzing water to produce a gas comprising hydrogen;
   an atomized/volatile gas generator, having a second casing remote from the first casing, the second casing accommodated with an atomized/volatile gas mixing tank for generating an atomized gas, the atomized gas selected from a group comprising water vapor, an atomized medicine, a volatile essential oil or any combination thereof; and
   a connector group removably coupled to the gas generator and the atomized/volatile gas generator, the connector group comprising a first single flexible pip; a second single flexible pipe and a mixed kit, wherein the first single flexible pipe is a sealed pipe directly connected between the mixed kit and the gas generator for transporting the gas comprising hydrogen from the gas generator to the mixed kit, the first single flexible pipe comprises a first end and a second end, the first end is removably and directly connected to the mixed kit, and the second end is removably and directly connected to the gas generator, the second single flexible pipe is a sealed pipe directly connected between the mixed kit and the atomized/volatile gas generator for transporting the atomized gas from the atomized/volatile gas generator to the mixed kit, the second single flexible pipe comprises a third end and a fourth end, the third end is removably and directly connected to the mixed kit, and the fourth end is removably and directly connected to the atomized/volatile gas generator, and the mixed kit mixes the gas comprising hydrogen and the atomized gas for generating a healthy gas and outputting the healthy gas.

2. The gas generating system for health use of claim 1, wherein the gas generator further comprises a humidifier, the humidifier is configured in the first casing and connected to the electrolysis device, the humidifier is used for receiving the gas comprising hydrogen to generate a filtered gas comprising hydrogen, and the healthy gas is mixed with the atomized gas and the filtered gas comprising hydrogen.

3. The gas generating system for health use of claim 2, wherein the gas generator further comprises a conversion valve, the conversion valve is configured between the humidifier and the atomized/volatile gas generator, and the conversion valve is adapted to be selectively connected from the humidifier to the atomized/volatile gas generator so that the atomized gas is mixed with the filtered gas comprising hydrogen in order to generate the healthy gas, or the conversion valve is adapted to be selectively disconnected from the humidifier to the atomized/volatile gas mixing tank so that the filtered gas comprising hydrogen is directly outputted from the first casing and provided to be inhaled by a user.

4. The gas generating system for health use of claim 1, wherein the atomized/volatile gas generator further comprises an oscillator, where the oscillator is used for atomizing or vaporizing a liquid in order to generate the atomized gas.

5. The gas generating system for health use of claim 4, wherein the liquid is selected from a group comprising an essential oil, a medicinal liquid, pure water or any combination thereof.

6. The gas generating system for health use of claim 5, wherein the atomized/volatile gas generator further comprises an atomized base liquid, the liquid is set above the atomized base liquid, and the oscillator is set under the atomized base liquid.

7. The gas generating system for health use of claim 1, further comprising a flow rate detection device coupled to the electrolysis device for detecting the flow rate of the gas comprising hydrogen and controlling the production capacity of the gas comprising hydrogen comprised in the electrolysis device.

8. The gas generating system for health use of claim 7, wherein the flow rate detection device can shut down an input voltage or an input current of the electrolysis device.

9. The gas generating system for health use of claim 1, further comprising a mask, wherein the mixed kit outputting the healthy gas through the mask.

* * * * *